US008304390B2

(12) United States Patent
Pfirrmann

(10) Patent No.: US 8,304,390 B2
(45) Date of Patent: *Nov. 6, 2012

(54) METHOD OF TREATMENT FOR PREVENTING OR REDUCING TUMOR GROWTH IN THE LIVER OF PATIENT

(75) Inventor: Rolf W. Pfirrmann, Lucerne (CH)

(73) Assignee: Ed. Geistlich Soehne AG fuer Chemische Industrie, Wolhusen (CH)

( * ) Notice: Subject to any disclaimer, the term of this patent is extended or adjusted under 35 U.S.C. 154(b) by 686 days.

This patent is subject to a terminal disclaimer.

(21) Appl. No.: 11/350,275

(22) Filed: Feb. 9, 2006

(65) Prior Publication Data
US 2006/0194796 A1 Aug. 31, 2006

Related U.S. Application Data

(60) Continuation-in-part of application No. 09/971,774, filed on Oct. 9, 2001, now Pat. No. 7,151,099, which is a continuation-in-part of application No. 09/493,797, filed on Jan. 28, 2000, now abandoned, which is a continuation of application No. PCT/GB98/02311, filed on Jul. 31, 1998, application No. 11/350,275, filed on Feb. 9, 2006, which is a continuation-in-part of application No. 10/424,102, filed on Apr. 28, 2003, now Pat. No. 7,638,511, which is a continuation of application No. 10/281,138, filed on Oct. 28, 2002, now Pat. No. 6,815,441, which is a division of application No. 09/583,902, filed on Jun. 1, 2000, now Pat. No. 6,479,481, which is a continuation-in-part of application No. 10/934,474, filed on Sep. 7, 2004, which is a continuation-in-part of application No. 10/109,058, filed on Mar. 29, 2002, now abandoned.

(60) Provisional application No. 60/137,421, filed on Jun. 4, 1999, provisional application No. 60/151,050, filed on Aug. 27, 1999, provisional application No. 60/167,681, filed on Nov. 29, 1999, provisional application No. 60/174,607, filed on Jan. 5, 2000, provisional application No. 60/182,200, filed on Feb. 14, 2000, provisional application No. 60/239,916, filed on Oct. 13, 2000, provisional application No. 60/246,100, filed on Nov. 7, 2000, provisional application No. 60/253,138, filed on Nov. 28, 2000, provisional application No. 60/280,748, filed on Apr. 3, 2001, provisional application No. 60/281,710, filed on Apr. 6, 2001, provisional application No. 60/281,711, filed on Apr. 6, 2001, provisional application No. 60/281,712, filed on Apr. 6, 2001, provisional application No. 60/281,713, filed on Apr. 6, 2001, provisional application No. 60/284,933, filed on Apr. 20, 2001, provisional application No. 60/284,934, filed on Apr. 20, 2001.

(30) Foreign Application Priority Data

Jul. 31, 1997 (GB) .................... 9716219.2

(51) Int. Cl.
A61K 38/19 (2006.01)
A61K 31/549 (2006.01)
(52) U.S. Cl. .................................... 514/18.9; 514/223.8
(58) Field of Classification Search ........................ None
See application file for complete search history.

(56) References Cited

U.S. PATENT DOCUMENTS

| 504,243 A | 8/1893 | Philippot |
| 1,039,140 A | 9/1912 | Kampfe |
| 1,188,697 A | 6/1916 | Steinberg |
| 1,461,366 A | 7/1923 | Mulford et al. |
| 1,676,146 A | 7/1928 | Krafft |
| 2,021,465 A | 11/1935 | Ritscher |
| 2,609,960 A | 9/1952 | Irwin |
| 2,643,024 A | 6/1953 | Cronheim |
| 2,760,672 A | 8/1956 | Cronheim |
| 3,598,105 A | 8/1971 | Cristaldi |
| 3,809,064 A | 5/1974 | Ziegler |
| 3,961,443 A | 6/1976 | Insalaco |
| 4,000,830 A | 1/1977 | French |
| 4,350,156 A | 9/1982 | Malchesky et al. |
| 4,467,784 A | 8/1984 | Lee et al. |
| 4,482,077 A | 11/1984 | Henderson |
| 4,626,536 A | 12/1986 | Pfirrmann |
| 4,654,345 A | 3/1987 | Cavanak |
| 4,828,140 A | 5/1989 | Henderson |
| 4,960,415 A | 10/1990 | Reinmüller |
| 5,077,281 A | 12/1991 | Reinmueller |
| 5,167,960 A | 12/1992 | Ito et al. |
| 5,176,651 A | 1/1993 | Allgood et al. |
| 5,191,900 A | 3/1993 | Mishra |
| 5,208,018 A | 5/1993 | Gough |
| 5,210,083 A | 5/1993 | Pfirrmann |
| 5,262,403 A | 11/1993 | Nicolson et al. |
| 5,362,754 A | 11/1994 | Raad et al. |
| 5,416,091 A | 5/1995 | King |
| 5,441,481 A | 8/1995 | Mishra et al. |
| 5,554,148 A | 9/1996 | Aebischer et al. |

(Continued)

FOREIGN PATENT DOCUMENTS
CA 2302720 A1 9/2000
(Continued)

OTHER PUBLICATIONS

Gugenheim, J. et al "Laparoscopic resection of solid liver tumours" Br. J. Surg. (1996) vol. 83, pp. 334-335.*

(Continued)

Primary Examiner — Leigh Maier
(74) Attorney, Agent, or Firm — Rothwell, Figg, Ernst & Manbeck, P.C.

(57) ABSTRACT

A method of treatment for preventing or reducing tumor growth in liver of a patient includes administering to the patient an effective about of taurolidine, taurultam or a mixture thereof, so as to prevent or reduce the tumor growth in the patient.

11 Claims, No Drawings

U.S. PATENT DOCUMENTS

| | | | |
|---|---|---|---|
| 5,593,665 A | 1/1997 | Pfirrmann et al. | |
| 5,696,153 A | 12/1997 | Ainsworth et al. | |
| 5,725,553 A | 3/1998 | Moenning | |
| 5,730,045 A | 3/1998 | Delaquis et al. | |
| 5,749,859 A | 5/1998 | Powell | |
| 5,763,421 A | 6/1998 | Caretto et al. | |
| 5,819,748 A | 10/1998 | Pfirrmann | |
| 5,881,905 A | 3/1999 | Brady | |
| 5,889,183 A | 3/1999 | Herdeis et al. | |
| 5,957,038 A | 9/1999 | Shimazaki | |
| 6,011,030 A | 1/2000 | Pfirrmann | |
| 6,029,843 A | 2/2000 | Kroscher et al. | |
| 6,030,358 A | 2/2000 | Odland | |
| 6,035,766 A | 3/2000 | Schirmer | |
| 6,080,397 A | 6/2000 | Pfirrmann | |
| 6,093,180 A | 7/2000 | Elsberry | |
| 6,105,811 A | 8/2000 | Alfred | |
| 6,117,868 A | 9/2000 | Pfirrmann | |
| 6,166,007 A | 12/2000 | Sodemann | |
| 6,258,797 B1 | 7/2001 | Lehner | |
| 6,303,596 B1 | 10/2001 | Morrissey et al. | |
| 6,429,224 B1 | 8/2002 | Calabresi et al. | |
| 6,451,759 B1* | 9/2002 | Kang et al. | 514/18.9 |
| 6,479,481 B1 | 11/2002 | Stendel et al. | |
| 6,521,616 B2 | 2/2003 | Calabresi et al. | |
| 6,546,849 B1 | 4/2003 | Shimazaki | |
| 6,617,333 B2 | 9/2003 | Rabindran et al. | |
| 6,688,487 B2 | 2/2004 | Oakes et al. | |
| 6,815,441 B2 | 11/2004 | Stendel et al. | |
| 6,821,968 B2 | 11/2004 | Pfirrmann | |
| 6,995,164 B2 | 2/2006 | Calabresi et al. | |
| 7,151,099 B2* | 12/2006 | Redmond et al. | 514/222.5 |
| 2001/0031870 A1 | 10/2001 | Soll et al. | |
| 2002/0052366 A1 | 5/2002 | Calabresi et al. | |
| 2002/0091123 A1* | 7/2002 | Redmond et al. | 514/222.5 |
| 2002/0098164 A1 | 7/2002 | Redmond et al. | |
| 2002/0111328 A1 | 8/2002 | Redmond et al. | |
| 2002/0111345 A1 | 8/2002 | Calabresi et al. | |
| 2002/0131935 A1 | 9/2002 | Fisher et al. | |
| 2003/0027818 A1 | 2/2003 | Redmond et al. | |
| 2003/0092707 A1 | 5/2003 | Redmond et al. | |
| 2003/0195198 A1 | 10/2003 | Stendel et al. | |
| 2004/0087579 A1 | 5/2004 | Redmond et al. | |

FOREIGN PATENT DOCUMENTS

| | | |
|---|---|---|
| CA | 2393159 A1 | 6/2001 |
| CA | 2393252 A1 | 6/2001 |
| CH | 587040 A5 | 4/1977 |
| DE | 3536560 A1 | 4/1986 |
| DE | 19606897 A1 | 8/1997 |
| EP | 0048558 A2 | 3/1982 |
| EP | 0139535 A2 | 5/1985 |
| EP | 0147021 A1 | 7/1985 |
| EP | 0253662 A1 | 1/1988 |
| EP | 1040841 A1 | 10/2000 |
| EP | 1066830 A2 | 1/2001 |
| EP | 1201247 A2 | 5/2002 |
| EP | 1247524 A1 | 10/2002 |
| GB | 2165752 A | 4/1986 |
| JP | 60-105618 A | 6/1985 |
| JP | 61-000017 A | 1/1986 |
| JP | 63-72626 A | 4/1988 |
| JP | 5-500973 A | 2/1993 |
| JP | 5-505615 A | 8/1993 |
| JP | 2000-300661 A | 10/2000 |
| JP | 2000-516196 A | 12/2000 |
| JP | 2001-10976 A | 1/2001 |
| JP | 2002-326936 A | 11/2002 |
| WO | WO 88/05301 | 7/1988 |
| WO | WO 91/13628 A1 | 9/1991 |
| WO | WO 92/00743 A1 | 1/1992 |
| WO | WO 95/18638 A1 | 7/1995 |
| WO | WO 95/30423 A2 | 11/1995 |
| WO | WO 97/25052 A2 | 7/1997 |
| WO | WO 98/28027 | 7/1998 |
| WO | WO 98/39354 A1 | 9/1998 |
| WO | WO 98/52572 A1 | 11/1998 |
| WO | WO 99/06114 A2 | 2/1999 |
| WO | WO 01/39762 A3 | 6/2001 |
| WO | WO 01/39763 A2 | 6/2001 |
| WO | WO 0207810 A2 | 1/2002 |

OTHER PUBLICATIONS

Lee, S. H. et al "Expression of Fas and Fas-related molecules . . . " Human Pathology (2001) vol. 32, No. 3, pp. 250-256.*

Bedrosian, I., et al., Taurolidine, an Analogue of the Amino Acid Taurine, Suppresses Interleukin 1 and Tumor Necrosis Factor Synthesis in Human Peripheral Blood Mononuclear Cells, Cytokine vol. 3, No. 6 Nov. 1991: 568-575.

Clark, K., et al., "KRN8602 (MX2-hydrochloride): an Active New Agent for the Treatment of Recurrent High-grade Glioma", J. Clin. Oncol., Aug. 1999, 17 (8): 2579-84, PUBMED Abstract.

Dimmock, Jr, et al., "Mannich Bases of Phenolic Azobenzenes Possessing Cytotoxic Activity", Eur. J. Med. Chem. (1997) 32, 583-594.

Jacobi, C.A., et al., "Intraperitoneal Instillation of Taurolidine and Heparin for the Prevention of Intraperitoneal Tumor Growth and Trocar Metastases in Laparoscopic Surgery in a Rat Model", Lagenbecks Arch Chir (1997) 382 [Suppl. 1]: S31-S36.

Jacobi, C.A., et al., "Inhibition of Peritoneal Tumor Cell Growth and Implantation in Laparoscopic Surgery in a Rat Model", Am J of Surgery, vol. 174, Sep. 1997: 359-363.

Monson, J.R.T., et al., "Taurolidine as an anti-neoplastic agent: a previously undiscovered role?", Br. J. Surg., vol. 77, No. 12, Dec. 1990, 1432.

Monson, J.R.T., et al., "Preliminary Evidence that Taurolidine is anti-neoplastic as well as anti-endotoxin and anti-microbial", Br. J. Surg., vol. 77, No. 6, Jun. 1990, A711.

Monson, J.R.T., et al., "Abrogation of tumor necrosis factor (TNF) toxicity in the murine model by taurolidine: support for synergism of TNF with endotoxin", Br. J. Surg., vol. 77, No. 6, Jun. 1990, A708.

Monson, J.R.T., et al., "Taurolidine inhibits tumour necrosis factor (TNF) toxicity—new evidence in TNF and endotoxin synergy?", Euro. J. Surg. Oncology, 1993; 19:226-231.

Kirsch, L., et al., "The Effect of Polyvinylpyrrolidine on the Stability of Taurolidine", Pharmaceutical Development and Technology, 2:4, 345-356 (1997).

Lucarotti, M. et al., "Antiseptic Toxicity to breast carcinoma in tissue culture an adjuvant to conservation therapy", Annals of the Royal College of Surgeons of England, (1990), vol. 72, 388-392.

Jacobi, C.A., et al., "Peritoneale Instillation von Taurolidin and Hepain zur Verhinderung von Intraperitorealem Tumorwachstum und Trokarmetastasen bei laparoskopischen Operationen im Rattenmodell", Langenbecks Arch Chir., vol. 382, Suppl. 1, pp. S31-S36 (1997).

Treutner, K., et al., "Prevention of Postoperative Adhesions by Single Intraperitoneal Medication", Journal of Surgical Research, vol. 59, pp. 764-771 (1995).

Embase abstract of J. Surg. Res. vol. 59;6, pp. 764-771, 1995.

Janik, Joseph S., et al., "Prevention of Postoperative Peritoneal Adhesions, Efficacy of Povidone", Arch Surg., vol. 117, pp. 1321-1324, (1982).

Kopple, JD, et al., "Effect of Intravenous Taurine Supplementation on Plasma, Blood Cell, and Urine Taurine Concentrations in Adults Undergoing Long-term Parenteral Nutrition", Am. J. Clin. Nutr., vol. 52, No. 5., (1990) Abstract.

Braumann, C., et al., "The Influence of Intraoperative Intravenous and Intraperitoneal Application of Taurolidine with Heparin on Subcutaneous and Intraperitoneal Tumor Growth in Laparoscopic Surgery in a Rat Model", Department of Surgery, Humboldt-University of Berlin, Campus Chartié Mitte, Schumannstr. 20-21, 10098 Berlin, Germany, Apr. 14th and 15th, 2000, 3 pages.

Jacobi, C.A., et al., "Influence of Different Gases and Intraperitoneal Instillation of Antiadherent or Cytotoxic Agents on Peritoneal Tumor Cell Growth and Implantation with Laparoscopic Surgery in a Rat Model", Surg Endosc, (1999) 13:1021-1025.

Jacobi, C.A., et al., "New Therapeutic Strategies to Avoid Intra-and Extraperitoneal Metastases during Laparoscopy: Results of a Tumor Model in the Rat", Dig Surg, 1999; 16:393-399.

Morgan-McCourt et al., Taurolodine inhibits tumor cell growth in vitro and in vivo, Annals of Surgical Oncology, Jul. 17, 2000, 685-691, vol. 7, No. 9, Lippincott Williams & Wilkins, Ireland.

Stendel, R. et al., "Enhancement of fas-ligand-mediated programmed cell death by taurolidine", Anticancer Research 23:2309-2314 (2003).

Anderson et al. (Journal of Clinical Investigation, 1996, vol. 97, pp. 1952-1959).

Edwards et al. (Journal of Clinical Investigation, 1992, vol. 90, pp. 637-641).

Abstract of Kimura et al. (Cancer, 1997, vol. 80, pp. 42-49).

The abstract of Jacobs et al. (Cancer Res. 1986, vol. 46, (4 pt 2), pp. 2101-2104).

Negrier et al. (Eur J. Cancer Clin. Oncol., 1989, vol. 25, suppl 3, pp. S21-S28).

Abstract of Salmaggi et al. (Italian Journal of Neurological Sciences, 1996, vol. 17, pp. 267-276).

Ananthan, in *Cancer Chemotherapeutic Agents*, Foye (Ed.), American Chem. Soc., Washington, D.C. (1995) pp. 49-58.

Anonymous, "Cerebrospinal Fluid" http://uscneurosurgery.com/infonet/glossary/c/cerebrospinal%20/fluid%20csf.htm. 2 pages. Accessed May 31, 2007.

Anonymous, "Methods of Sterilisation." *British Pharmacopoeia*. vol. 2, Appendix XVIII: A264-A267, 1998.

Anonymous, "Taurolin Suppresses Activity of Tumor Necrosis Factor-$\alpha$ in vivo", Institute of Pharmacology, University of Zurich, Research Report, 1-9, 1993.

Araki et al., *J. Jap. Soc. Gastroenterol. Surg.* 27(5): 1090-1093, 1994.

Blenkharn, "The Antimicrobial Activity of Taurolin®—a Possible New Additive for Parenteral Nutrition Solutions", *Clin. Nutr.* 6(1): 35-38, 1987.

Blum et al., "Hexamethylmelamine—A New Drug with Activity in Solid Tumors", *Eur. J. Cancer*, 9:195-202, 1973.

Braumann et al., "Influence of intraperitoneal and systemic application of taurolidine and taurolidine/heparin during laparoscopy on intraperitoneal and subcutaneous tumour growth in rats", *Clin. Exp. Metastasis* 18: 547-552, 2001.

Braumann et al., "Local and systemic chemotherapy with taurolidine and taurolidine/heparin in colon cancer-bearing rats undergoing laparotomy", *Clin. Exp. Metastasis*, 20: 387-394, 2003.

Braumann et al., "The Tumor-Suppressive Reagent Taurolidine is an Inhibitor of Protein Biosynthesis", *Int. J. Cancer*, 112: 225-230, 2004.

Braumann et al., "Effects of increasing doses of a bolus injection and an intravenous long-term therapy of taurolidine on subcutaneous (metastatic) tumor growth in rats", *Clin. Exp. Metastasis*, 22: 77-83, 2005.

Braumann et al., "High Doses of Taurolidine Inhibit Advanced Intraperitoneal Tumor Growth in Rats", *J. Surg. Res.* 129: 129-135, 2005.

Braumann et al., "Prevention of disease progression in a patient with a gastric cancer-re-recurrence. Outcome after intravenous treatment with the novel antineoplastic agent taurolidine. Report of a case", *World J. Surg. Oncol.* 4(34): 6 pages, 2006.

Calabresi et al., "Taurolidine: Cytotoxic and Mechanistic Evaluation of a Novel Antineoplastic Agent", *Can. Res.* 61: 6816-6821, 2001.

Campbell et al., "The Role of Tumor Rejection Antigens in Host Antitumor Defense Mechanisms", *Cancer*, 75(11): 2649-2655, 1995.

Carter et al., *Chemotherapy of Cancer*, Second Ed., John Wiley & Sons, New York, 71-78, 1981.

Da Costa et al., "The effect of laparotomy and laparoscopy on the establishment of spontaneous tumor metastases", *Surgery*, 124(3): 516-525, 1998.

Da Costa et al., "Laparotomy and laparoscopy differentially accelerate experimental flank tumour growth", *Br. J. Surg.* 85: 1439-1442, 1998.

Da Costa et al., "Taurolidine Improves Survival by Abrogating the Accelerated Development and Proliferation of Solid Tumors and Development of Organ Metastases from Circulating Tumor Cells Released Following Surgery" *J. Surg. Res.* 101:111-119, 2001.

Darnowski et al., "Mechanistic and antineoplastic evaluation of taurolidine in the DU145 model of human prostate cancer", *Can. Chemother. Pharmacol*, 54: 249-258, 2004.

Endoh, "Effects of Recombinant Interleukin-2 (rIL-2) for Recurrent and Metastatic Renal Cell Carcinoma", *Biotherapy*, 5(6): 1100-1106, 1991.

Erb et al., "Structural Investigation of a New Organic Antiseptic: Taurolidine", *Talanta*, 29: 953-958, 1982.

Erb et al., "Structural investigation of a new organic antiseptic: Taurolidine Analytical study and application to identification and quantitation in biological fluids", *Eur. J. Drug Metab. Pharm.* 8(2): 163-173, 1983.

Fanning et al., "Inhibition of neutrophils apoptosis after elective surgery", *Surgery*, pp. 527-534, 1999.

Fiedler, in *Lexikon der Hilfsstoffe für Pharmazie, Kosmetik und andrenzende Gebiete*, Editio Cantor Aulendorf, 695, 1985.

Finnegan et al., "Taurine Attenuates Recombinant Interleukin-2-Activated, Lymphocyte-Mediated Endothelial Cell Injury", *Cancer*, 82(1): 186-199, 1998.

Fukushima, "Merck Manual, $17^{th}$ Edition in Japanese", Nikkei BP, pp. 983-992, 1999 (partial English translation).

Gallagher et al., "Hepatic Resection of Solitary Metastasis from Transitional Cell Carcinoma of the Bladder", *J. Urology*, 159: 986, 1998.

Gavrovskaya et al., "Antihypoxic Properties of Taurinamide Derivatives: The Experimental Study", *Taurine*, 6: 523-528, 2006.

Glesby et al., "Pilot Study of Low Dose Daily Interleukin-2 Plus Pegylated-Interferon-alfa-2b and Ribavirin in Patients with HCV/HIV Co-infection: ACTG A5088", $11^{th}$ Conf. Retrovir Opportunistic Infect., Abstract 818, 1-2, 2004.

Hansen et al., "Altretamine", *The Annals of Pharmacotherapy*, 25:146-152, 1991.

Hood et al., "Studies of the thiadiazine, Taurolidine- I. Identification of the Molecular Species Present in Aqueous Solutions by $^1$H- and $^{13}$C-NMR Spectroscopy", *Talanta*, 41(1): 107-113,1994.

Huscher et al., "Laparoscopic Colorectal Resection", *Surg. Endosc.* 10: 875-879, 1996.

Jacobi et al., "Taurolidine- a new drug with anti-tumor and anti-angiogenic effects", *Anti-Cancer Drugs*, 16(9): 917-921, 2005.

Japanese Office Action for JP appln 2002-280476 entitled "Preliminary Notice of Reasons for Rejection", Dec. 4, 2008, and English language translation, pp. 1-7.

Johnston et al., "Taurolin for the Prevention of Parenternal Nutrition Related Infection: Antimicrobial Activity and Long-Term Use", *Clin. Nutr.* 12(6): 365-368, 1993.

Kilian et al., "Effects of taurolidine and octreotide on tumor growth and lipid peroxidation after staging-laparoscopy in ductal pancreatic cancer", *Prostaglandins, Leukotrienes and Essential Fatty Acids*, 69: 261-267, 2003.

Kilian et al., "Impact of taurolidin and octreotide on liver metastasis and lipid peroxidation after laparoscopy in chemical induced ductal pancreatic cancer", *Investigational New Drugs*, 23: 157-164, 2005.

Koike et al., "Effect of 48-hour Continuous Intravenous Injection of 5-Flouorouracil (5-FU) for Hematogenous Metastasis of Large Intestine Carcinoma", *Jap. J. Gastro. Surg.* 24(2): 1-3, 1991 (partial English translation).

Koldehoff et al., "Taurolidine is effective in the treatment of central venous catheter-related bloodstream infections in cancer patients", *Intl. J. Antimicrobial Agents*, 24: 491-495, 2004.

McNamara et al., "Significance of angiogenesis in cancer therapy", *Br. J. Surg.* 85: 1044-1055, 1998.

Medical Encyclopedia: Electrolytes http://www.nlm.nih.gov/medlineplus/ency/article/002350.htm, 1, 2001. Accessed May 31, 2007.

Medical Encyclopedia: Protein in diet http://www.nlm.nih.gov/medlineplus/print/ency/article/002467.htm, 1-2, 2001. Accessed May 31, 2007.

Monson, "Malignant Melanoma: A Plague of our Times", *Br. J. Surg.*, 76: 997-998, 1989.

Mughal et al., "Infected Feeding Lines", *Care Critically III* 6(6): 228-231, 1990.

Nestler et al., "Impact of taurolidine on the growth of CC531 colon carcinoma cells in vitro and in a laparoscopic animal model in rats", *Surg. Endosc.*, 19: 280-284, 2005.

Nici et al., "The Effects of Taurolidine, a Novel Antineoplastic Agent, on Human Malignant Mesothelioma", *Clin. Can. Res.* 10: 7655-7661, 2004.

Nudelman et al., "Prodrugs of butyric acid. Novel derivatives possessing increased aqueous solubility and potential for treating cancer and blood diseases", *Eur. J. Med. Chem.* 36: 63-74, 2001.

O'Brien et al., "Co-immunotherapy with interleukin-2 and taurolidine for progressive metastatic melanoma", *Irish J. Med. Sci.* 175(1): 10-15, 2006.

Okuno et al., "Intrahepatic interleukin-2 with chemotherapy for unresectable liver metastases: a randomized multicenter trial" *Hepato-Gastroenterology*, 46(26): 1116-21, Abstract, 1 pg., 1999.

Opitz et al., "The influence of adhesion prophylactic substances and taurolidine/heparin on local recurrence and intraperitoneal tumor growth after laparoscopic-assisted bowel resection of colon carcinoma in a rat model" Surg. Endosc. 17:1098-1104, 2003.

Opitz et al., "Instillation of Taurolidine/Heparin after Laparotomy Reduces Intraperitoneal Tumour Growth in a Colon Cancer Rat Model", *Eur. Surg. Res.* 39: 129-135, 2007.

Opitz et al., "Taurolidine and povidone-iodine induce different types of cell death in malignant pleural mesothelioma" *Lung Cancer*, 56: 327-336, 2007.

Opitz et al., "Local recurrence model of malignant pleural mesothelioma for investigation of intrapleural treatment", *Eur. J. Cardio-thoracic Surg.* 31: 772-778, 2007.

Parfitt, "Martindale, the complete drug reference, 32$^{nd}$ ed", (formerly Martindale the extra pharmacopoeia), London: Pharmacopoeia), XP-002231711, London: Pharmaceutical press, GB, 534-537, 1999.

Physicians' Desk Reference, "Fluorouracil Product Information", pp. 2034-2036, 1995.

Pidgeon et al., "The role of endotoxin/lipopolysaccharide in surgically induced tumour growth in a murine model of metastatic disease", *Br. J. Can.* 81(8): 1311-1317, 1999.

Redmond et al., Letter to the Editor, *Annals of Surgery*, 227(2): 309, 1998.

Reinmueller, "Die Beeinflussung der physiologischen und pathologischen Gerinnung durch Taurolidin und Implikationen für die Anwendung", *Zentralbl Chir Suppl*, 4: 13-18, 1999.

Reymond et al., "Feasibility of therapeutic pneumoperitoneum in a large animal model using a microvaporisator", *Surg. Endosc.*, 14: 51-55, 2000.

Ribizzi et al., "Taurolidine: preclinical evaluation of a novel, highly selective, agent for bone marrow purging", *Bone Marrow Transplantation*, 29: 313-319, 2002.

Rodak et al., "Induction of reactive oxygen intermediates-dependent programmed cell death in human malignant ex vivo glioma cells and inhibition of the vascular endothelial growth factor production by taurolidine", *J. Neurosurg.*, 102: 1055-1068, 2005.

Semple et al., "Potent and Selective Thrombin Inhibitors Featuring Hydrophobic, Basic $P_3$-$P_4$-aminoalkyllactam Moieties", *Bioorganic & Medicinal Chemistry Let.* 8: 3525-3530, 1998.

Shrayer et al., "The effect of Taurolidine on adherent and floating subpopulations of melanoma cells", *Anti-Cancer Drugs*, 14(4): 295-303, 2003.

Simon et al., "Diagnosis and treatment of catheter-related infections in paediatric oncology: and update", *Clin. Microbiol. Infect.*, 12(7): 606-620, 2006.

Smith, "Interleukin 2 Toxicity—Standard Procedures for Recording & Reporting Drug Toxicities", 1-8, 2000.

Smith et al., "New Strategies to Combat HIV: Augmenting Antiviral Immunity, Rationale for Low-Dose Daily IL-2 Therapy", *AIDS Read.* 13(8): 365-369, 382, 2003.

Stapleton et al., "Taurine and Inflammation—A New Approach to an Old Problem?" *J. of Leukocyte Biol.*, 61: 231-232, 1997.

Stendel et al., "The Effect of Taurolidine on Brain Tumor Cells", *Anticancer Research*, 22: 809-814, 2002.

Stendel et al., "Taurolidine-Fibrin-Sealant-Matrix Using Spray Application for Local Treatment of Brain Tumors", *Antican. Res.* 24: 631-638, 2004.

Stendel et al., "Treatment of Glioblastoma with Intravenous Taurolidine. First Clinical Experience", *Antican. Res.* 24: 1143-1148, 2004.

Stendel et al., "Pharmacokinetics of Taurolidine following Repeated Intravenous Infusions Measured by HPLC-ESI-MS?MS of the Derivatives Taurultame and Taurinamide in Glioblastoma Patients", *Clin. Pharmacokinet*, 46(6): 513-524, 2007.

Sun et al., "Taurolidine Induces Apoptosis of Murine Melanoma Cells in Vitro and in Vivo by Modulation of the Bcl-2 Family Proteins", *J. Sur. Oncol.* 96: 241-248, 2007.

Suzuki et al., "Am Effective Case of Combined Arterial and Portal Infusion Chemotherapy for Sigmoid Colon Cancer with Multiple Liver Metastases", *Jap. Soc. Gastroent. Surg.* 27(5): 1090-1093, 1994.

Thatcher et al., "Recombinant interleukin-2 (rlL-2) given intrasplenically and intravenously for advanced malignant melanoma. A phase I and II study", *Br. J. Cancer*, 60: 770-774, 1989.

University of Florida Shands Cancer Center: "Electrolyte Imbalance", http://www/ufscc.ufl.edu/Patient/content.aspx?section=ufscc &id-213137 (2006). Accessed May 4, 2006.

Van Gelder, "A Central Mechanism of Action for Taurine: Osmoregulation, Bivalent Cations, and Excitation Threshold", *Neurochem. Res.* 8(5): 687-699, 1983.

Volz, et al., "Modulation of Tumor-Induced Lethality after Pneumoperitoneum in a Mouse Model", *Cancer*, 89(2): 262-266, 2000.

Wakabayashi et al., "Chemotherapy for Brain Tumors", 50(2): 305-312, 2001 (partial English translation).

Wang et al., "Endotoxin/Lipopolysaccharide Activates NF-kB and Enhances Tumor Cell Adhesion and Invasion Through a β1 Integrin-Dependent Mechanism", *J. Immunol.*, vol. 170, pp. 795-804, 2003.

Watson et al., "Taurolidine, an antilipopolysaccharide agent, has immunoregulatory properties that are mediated by the amino acid taurine", *J. Leukocyte Biol.* 58: 299-306, 1995.

Weberschock et al., "Efficacy of Sytemic [sic] Taurolidin Application in the Treatment of Liver Metastases in a Rat Model", Dept. of General and Vascular Surgery, Johann Wolfgang Goethe University, 1 page, 1996-2002 (Abstract).

Wenger et al., "Effects of taurolidine and octreotide on port site and liver metastasis after laparoscopy in an animal model of pancreatic cancer", *Clin. & Exp. Metastasis*, 19: 169-173, 2002.

Wicki et al., *Taurolin—A New Concept in Antimicorbial Chemotherapy in Surgical Infection*, Urban & Schwarzenberg, Munich, 3:244-253, 1985.

Wittich et al., "Irrigation of Port Sites: Prevention of Port Site Metastases?" *J. Laparoendoscopic & Advanced Surg. Tech.* 14(3): 125-129, 2004.

Wördemann et al., "Tumor Necrosis Factor-α Production by Human Hepatoma Cell Lines is Resistant to Drugs That Are Inhibitory to Macrophages", *J. Interf. and Cytokine Res.* 18: 1069-1075, 1998.

Wu et al., "Neutrophil-induced Transmigration of Tumour Cells Treated with Tumour-conditioned Medium is Facilitated by Granulocyte-macrophage Colony-stimulating Factor", *Eur. J. Surg.*, 166: 321-366, 2000.

Lubec et al. "Decreased Tumor Incidence and Increased Survival by One Year Oral Low Dose Arginine Supplementation in the Mouse" Life Sci. 58(25):2317-2325, 1996.

* cited by examiner

METHOD OF TREATMENT FOR PREVENTING OR REDUCING TUMOR GROWTH IN THE LIVER OF PATIENT

CROSS-REFERENCE TO RELATED APPLICATIONS

The present application is a continuation-in-part of U.S. application Ser. No. 09/971,774, filed Oct. 9, 2001, which is a continuation-in-part of U.S. application Ser. No. 09/493, 797, filed Jan. 28, 2000, which is a continuation of International Application No. PCT/GB98/02311, filed Jul. 31, 1998, and which claims foreign priority from GB 97 16219.2, filed Jul. 31, 1997. U.S. application Ser. No. 09/493,797 also claims the benefit of U.S. Provisional Application Ser. No. 60/239,916, filed Oct. 13, 2000, U.S. Provisional Application Ser. No. 60/246,100, filed Nov. 7, 2000 and U.S. Provisional Application Ser. No. 60/253,138, filed Nov. 28, 2000. This application also is a continuation-in-part of pending U.S. application Ser. No. 10/424,102, filed Apr. 28, 2003, which is a continuation of U.S. application Ser. No. 10/281,138, filed Oct. 28, 2002, now U.S. Pat. No. 6,815,441, which is a divisional of U.S. application Ser. No. 09/583,902, filed Jun. 1, 2000, now U.S. Pat. No. 6,479,481, which claims the benefit of U.S. Provisional Application No. 60/137,421 filed Jun. 4, 1999, and which claims the benefit of U.S. Provisional Application No. 60/151,050 filed Aug. 27, 1999, and which claims the benefit of U.S. Provisional Application No. 60/167,681 filed Nov. 29, 1999, and which claims the benefit of U.S. Provisional Application No. 60/174,607, filed Jan. 5, 2000 and which claims the benefit of U.S. Provisional Application No. 60/182,200 filed Feb. 14, 2000. This application also continuation-in-part of U.S. application Ser. No. 10/934,474, filed Sep. 7, 2004, which is a continuation-in-part of U.S. application Ser. No. 10/109,058, filed Mar. 29, 2002 which also claims the benefit of U.S. Provisional Application No. 60/280,748, filed Apr. 3, 2001, U.S. Provisional Application No. 60/281,710, filed Apr. 6, 2001, U.S. Provisional Application No. 60/281,711, filed Apr. 6, 2001, U.S. Provisional Application No. 60/281,712, filed Apr. 6, 2001, U.S. Provisional Application No. 60/281,713, filed Apr. 6, 2001, U.S. Provisional Application No. 60/284,933, filed Apr. 20, 2001, and U.S. Provisional Application No. 60/284,934, filed Apr. 20, 2001.

BACKGROUND OF THE INVENTION

1. Field of the Invention

The present invention relates to a method of treatment for preventing or reducing tumor growth in the liver of a patient.

2. Description of the Background Art

Prior art cancer treatments typically involve surgical removal of the cancerous tumor and subsequent treatment with anti-cancer drugs or radiation.

SUMMARY OF THE INVENTION

In accordance with the present invention, a method of treatment for preventing or reducing tumor growth in liver of a patient comprises administering to the patient an effective amount of taurolidine, taurultam or a mixture thereof, so as to prevent or reduce the tumor growth in the patient.

DETAILED DESCRIPTION OF THE INVENTION

According to one embodiment, a method of treatment for preventing or reducing tumor growth in liver of a patient comprises administering to the patient an effective amount of taurolidine, taurultam or a mixture thereof, so as to prevent or reduce said tumor growth in said patient. According to one embodiment, the tumor is a tumor metastases in said liver. The invention is applicable to patients having decompensated liver function or substantial liver failure. In certain embodiments, the liver tumor being treated in accordance with the present invention results from infiltration of stomach tumors into the liver, tumor metastases in the liver derived from cancer of the head of the pancreas, progressive carcinoma of the caecum, primary and/or recurrent cancer of the cardiac portion of the stomach, carcinoma of the kidneys and/or prostate, pancreatic cancer including pancreas carcinoma, peritoneal carcinosis, stomach cancer including gastric cancer, in the like.

According to one embodiment, the present invention relates to a method of treating abdominal cancer comprising performing a surgery on a patient's abdomen by forming a surgical opening in the patent's abdomen, and surgically removing a cancerous tumor from the patient's abdomen through the surgical opening. Prior to closing the surgical opening, taurolidine, taurultam or a mixture thereof is administered to the patient's abdomen so as to treat cancer in the patient's abdomen. After the surgical opening in the patient's abdomen is closed, additional taurolidine, taurultam or a mixture thereof is administered to the patient. In certain embodiments, taurolidine, taurultam or a mixture thereof also is administered to the patient prior to performing the surgery to remove the tumor. Exemplary abdominal cancers include, but are not limited to, colon cancer, rectal cancer, pancreatic cancer, stomach cancer and lung cancer. Taurolidine, taurultam and mixtures thereof have been found to have anti-angiogenic activity when administered pre-operatively, peri-operatively and post-operatively in conjunction with transabdominal oncology surgery. In accordance with one embodiment, the taurolidine and/or taurultam may be administered in combination with administration of 5-fluorouracil (5-FU), wherein the 5-FU is administered at a dosage within the range of about 0.1-1000 mg per dosage unit.

This invention also relates to a method for preventing metastases, in particular to a method for preventing metastatic growth of malignant tumors. More particularly it relates to a method for preventing metastatic growth following surgery, and especially minimally invasive abdominal surgery, such as endoscopic, e.g. laparoscopic surgery.

Malignant tumors within the body, and particularly the abdomen are frequently removed surgically. The exploration and excision of tumors by major invasive surgery has been used for many years, but, more recently, minimal invasive surgery has increasingly been used.

A wide range of indications of malignant tumors exist for which invasive surgery, such as laparotomy or laparoscopy, may used. These include, but are not restricted to, the following: oesophagus carcinoma (plaster cell carcinoma, adenocarcinoma) and cardiacarcinoma; malignant degenerative ulcus; carcinoma of the stomach, antrum or corpus, malign adenoma of island cells, re-section or total gastrecomy; carcinoma of the gall duct or distal choledochus; carcinoma of the pancreas head, papilla, corpus or cauda; carcinoma of the small or large intestinal tract, sarcoma; colon malignancy; adeno carcinoma, lymphoma, malign carcinoid, melanoma, fibrosarcoma; carcinoma of the rectum; ovarial carcinoma; mama carcinoma; and prostate carcinoma.

The use of minimal invasive surgery has brought with it a reduced mortality and a reduced post-operative infection rate. Classic open abdominal surgery, or laparotomy, for example, may require less operation time than minimal invasive surgery, but involves long post-operative convalescence and a greater risk of infection, e.g. sepsis. One reason why minimal invasive laparoscopies are on the increase is the drastically reduced amount of time that the patient needs to spend recuperating both in hospital and at home. Laparoscopy also has the advantage that there is a significant reduction in wound scars and in post-operative complications associated with wound healing.

A wide range of laparoscopic procedures are in general use, including laparoscopic cholecystectomy, laparoscopic fundoplicatio (anti-reflex surgery for gastro-oesophageal disease), laparoscopic treatment of para-oesophageal hernia, laparoscopic treatment of abdominal cysts (e.g. liver cysts removed by cystectomy), laparoscopic liver re-section, laparoscopic appendectomy, laparoscopic treatment of intestinal obstruction (e.g. incarcerated hernias, colon obstruction and massively dilated small bowel obstruction), laparoscopic colo-rectal surgery (e.g. ileosacral re-section, hemicolectomy, sigma-resection, rectum prolapse and rectum amputation), laparoscopic adhesiolysis, emergency laparoscopy (explorative diagnosis), differential diagnosis of appendicitis, acute abdomen, ileus, abdominal trauma, and oncological queries (e.g. to determine whether or not carcinoma is operable).

One aspect of minimally invasive laparoscopies which gives rise to concern, particularly when these are used to combat abdominal malignancies, is the extent to which metastatic growth has been observed. It is now recognised that manipulation of a malignancy can result in a disturbance and release of malignant cells which can then travel to other locations where, if they adhere and start growing, form metastases with predictably unfortunate results. This risk is lower during a classic open laparotomy, for example, so that the whole tumour is carefully excised and removed without transferring any cells to other parts of the abdomen. In a minimally invasive laparoscopy using a trocar, however, this may not be possible and disturbance of the tumour and its contact with adjacent tissues whilst being removed are inevitable. It has been found that "trocar metastases" are often a result of minimally invasive abdominal surgical procedures, e.g. laparoscopic surgery.

One reason for the frequent observation of metastases following laparoscopic intervention is believed to reside in the use of the trocar tubes or sleeves, the diameters of which may range from 5 to 20 mm. These can either result in damage to malignant tissues or may otherwise come into contact with cell-rich exudate which then drips from the trocar sleeve into the abdominal cavity thereby initiating metastases. To effect the removal of re-sected organs or pieces from the abdomen, a "rescue" bag is introduced via the trocar sleeve. This is particularly so when removing inflamed re-sections or neoplastic tissue in an attempt to prevent contamination of the abdominal cavity by re-sected neoplastic cells or cell threads of the primary tumour.

We have now found that the incidence of metastases following surgery, and in particular trocar metastases believed to be caused by laparoscopic operations, can be reduced if the area affected during the operation and any other internal tissue or organ with which any of the apparatus or tumour comes into contact is instilled with a solution containing taurultam, taurolidine or a mixture thereof.

In studies that have been carried out on animal models, a significant suppression in the growth or spread of tumours following instillation of taurultam or taurolidine has been observed.

Accordingly, viewed from one aspect, we provide the use of taurultam or taurolidine solutions to prevent or reduce metastatic growth. This is of particular application in preventing or reducing the incidence of metastatic growth following surgery, and particularly following the use of trocars during minimal invasive laparoscopic surgery, but has general application.

The present invention also relates to a method of treating abdominal cancer comprising performing a surgery on a patient's abdomen by forming a surgical opening in the patent's abdomen, surgically removing a cancerous tumor from the patient's abdomen through the surgical opening. Prior to opening the surgical opening, taurolidine, taurultam or a mixture thereof is administered to the patient's abdomen so as to treat cancer in the patient's abdomen. After the surgical opening in the patient's abdomen is closed, additional taurolidine, taurultam or a mixture thereof is administered to the patient. Exemplary abdominal cancers include, but are not limited to, colon cancer, rectal cancer, pancreatic cancer, stomach cancer and lung cancer. Taurolidine, taurultam and mixtures thereof have been found to have anti-angiogenic activity when administered pre-operatively, peri-operatively and post-operatively in conjunction with transabdominal oncology surgery.

Viewed from a further aspect, we provide the use taurolidine and/or taurultam in the manufacture of a medicament for the prevention of metastases, in particular for the prevention or reduction of metastatic growth.

A preferred solution will contain from 0.5 to 3% by weight of taurolidine, or from 2 to 3% by weight taurultam, depending on the solubility of the compound. Solutions containing from 0.5 to 1.0% or 2.0% taurolidine are preferred.

The solutions will generally be made up in sterile pyrogen-free water and may also contain, for example, inorganic or other salts or other components to render them isotonic. Parenterally acceptable polyols may, for example, also be present since these have been observed to increase the overall intravenous tolerance of taurolidine. Suitable polyols include carbohydrates, e.g. hexoses such as glucose and fructose (or mixtures of these such as invert sugar), pentoses such as xylose or polysaccharides such as dextran or hydrolysed starch; glycerol and sugar alcohols such as sorbitol, mannitol or xylitol.

The concentration of the polyol can usefully be in the range 3-40% by weight. In the case of glucose, the concentration may be in the range 10-30% by weight, preferably 20%.

The solutions may also contain polyvinylpyrrolidone (PVP). This may be incorporated into the solutions at a concentration of, e.g. from 4 to 7% by weight. A solution containing 5% PVP is preferred. This assists in solubilising the active substance and contributes also to the oncotic pressure of the solution. The molecular weight of the PVP should not be greater than 30,000 and is preferably less than 10,000, for example between 7000 and 9000. Kollidone 17 as sold by BASF is relatively quickly resorbed and excreted renally.

The exact mode of action of taurolidine or taurultam in preventing metastatic growth under these circumstances is still not known. Without wishing to be bound by theoretical considerations, we believe that the taurolidine or taurultam is capable of altering the protein structure surface of the adhesion molecules (receptors) such as I-P-selectine and fibronectine. It is believed that over-expression of molecules such as these, and including also integrine, vitronectine and laminin, are the principal cause of metastatic development since they are believed to provide the malignant cells with the ability to migrate and adhere to other cell surfaces and endothelium, in particular to vascular endothels. The malignant cells then become sedentary, allowing themselves to grow and further develop (metastases). Once developed, such cells are able to reach every organ either through the haematogenic or lymphatic channels (formation of metastases).

Taurolidine and/or taurultam may modify the surface structure of the malignant cell in such a way that over-expression of the adhesion molecules is reduced. As a result, adhesion of the malignant cells to other cell surfaces and endothelium, e.g. to endothels, is reduced or does not occur before the cell itself dies. Taurolidine or taurultam is also believed to prevent high cytokine levels, e.g. IL-1β, in peritoneal fluid, which in turn prevents tumor cell proliferation and adhesions.

The taurolidine or taurultam solution may be used simply by instillation, as an aerosol (a nebulised solution of taurolidine or taurultam) and/or by intravenous infusion. When being used in conjunction with a surgical procedure, it may be administered either prior to, during or after the surgical procedure being carried out. If used as an instillation to irrigate the surgically affected area, it will be administered intraoperatively or before closure of the surgical incision. In minimal invasive surgery, the solution can be passed through the trocar tubes or sleeves.

In general, in preparation for laparoscopy the abdominal wall is lifted. This may be achieved either by insulation (pneumoperitoneum) or mechanically. Special instruments are required to raise the abdominal wall without causing damage to the intestinal loops. A Veres needle having an opening on one side through which a gas may enter the abdominal cavity is generally used for preparation of the pneumoperitoneum. Gases conventionally used for insufflation include $N_2O$, $CO_2$ and helium which may be introduced into the abdominal cavity at a rate of up to 1 liter/min. Depending on the patient's body size and tissue tension, between 3 and 5 liters of $CO_2$ gas may be required. For diagnostic laparoscopy under local anesthetic, $N_2O$ is preferred since, unlike $CO_2$, this does not irritate the peritoneum. Whilst not wishing to be bound by theory, it is believed that this irritation could be one of the reasons for the more frequent appearance of metastases observed when using $CO_2$.

A metal suspension bar is conveniently used to lift the abdominal wall mechanically. Once inserted into the abdomen, special hooks are attached to the suspension bar and the abdomen is then raised using a chain and suspension scale.

According to the type of surgical procedure, for example in minimally invasive abdominal surgery, from 100-1000 ml, preferably from 100-250 ml, of a 2%, 1% or 0.5% taurolidine solution can be instilled at body temperature and allowed to remain in the abdominal cavity after the end of the operative procedure, and before extraction of the gas used in the pneumoperitoneum (which enlarges the abdominal cavity and with which the laparoscopy starts) and final removal of the trocar.

For the prophylaxis of post-operative complications, particularly trocar metastases, a 2% Taurolin, a 0.5% Taurolin-Ringer or a 2-3% taurultam solution may be used. Conveniently, the abdomen is rinsed with such a solution using a rinse-suction tube. A 5 or 10 liter rinse bag is filled with the desired rinse solution (isotonic saline or ringer solution) and hung at a height of approx. 2 m. 1-2 liters of rinse solution are then introduced through the rinse-suction tube. Following a short contact time (sufficient to ensure that the intestinal loops are completely covered by the rinse solution) the solution is then suctioned off. In cases of severe inflammation, the rinsing solution will appear opaque such that abdominal visibility using the optic and camera is poor. In such cases, this rinsing procedure must be repeated until the liquid in the abdomen is clear and translucent.

When the rinsing procedure is complete and the solution is clear, the rinse bag is then filled with 250 ml 2% Taurolin (pre-warmed to 37° C.) which is allowed to flow into the abdominal cavity. Finally, a drain is inserted before closure of the abdomen. In severe cases, e.g. severe peritonitis, it is possible to instill (and in some cases to leave) up to 1000 ml Taurolin 2% solution within the abdominal cavity. In place of a 2% Taurolin solution, 1-1.5 liters Taurolin-Ringer 0.5% solution or a 2-3% taurultam solution may be used.

In patients with malignant tumours it is particularly advantageous to additionally administer Taurolin 2% intravenously through a central catheter as a drop infusion, e.g. at a dosage of 4×250 ml per day). If necessary, the drop infusion may be continued for 2-3 days following surgery.

Thus, according to certain embodiments, the invention includes the step of administering taurolidine, taurultam or a mixture thereof to the patient after removal of the tumor and after closing of the surgical opening.

Alternatively, the 2% Taurolin solution may be instilled and suctioned off using a pressure-rinse apparatus. Another variation is to attach a pressure-cuff to the rinse bag whereby suction may be carried out using a suction-off apparatus. It is also possible to use an infusion pump as an alternative to instillation.

In certain embodiments, taurolidine, taurultam or a mixture thereof also is administered to the patient prior to performing the surgery to remove the tumor.

In one embodiment of the invention, the taurolidine or taurultam solution will be used simultaneously with heparin. The use of heparin alone has not been found significantly to influence metastatic growth but the use of heparin in conjunction with taurolidine, administered either in combination or separately, has been found to give a significant, synergistic effect. The desired dosage of heparin depends on the result of the blood coagulation test. Thus, this will vary from patient to patient but can nevertheless be readily determined by those skilled in the art. An average dosage of heparin can be expected to be in the range of from 230 to 625 I.U. heparin-Na/kg bodyweight. In general, 5000 I.U. heparin-Na might be administered up to 2 hours prior to surgery.

For use in laparoscopic surgery, standard-heparin-sodium or standard-heparin-calcium may be added to the taurolidine solution immediately prior to application. Alternatively, low molecular weight heparin may be used. Typically, 200-500 ml 0.5-1.0% Taurolin in isotonic saline or Ringer-solution may be administered in combination with 1000-5000 I.U. heparin via a trocar tube.

The taurolidine-heparin solution may conveniently be applied under pressure, e.g. approx. 10-12 mm Hg, by means of a micro-pump. Administered in this way, the solution enters the abdominal cavity as an aerosol, resulting in a more widespread application of the solution to all exposed interabdominal (interior and lateral) surfaces during surgery. Administration of the solution as an aerosol also results in an increased efficacy during pneumoperitoneum with carbon dioxide.

In an alternative embodiment of the invention, the taurolidine or taurultam solution may be used simultaneously with hyaluronic acid, e.g. with a 0.1% hyaluronic acid sodium salts pharmaceutical grade solution, preferably having a molecular weight of $2.5 \times 10^6$ Da.

In accordance with one embodiment, the taurolidine and/or taurultam may be administered in combination with administration of 5-fluorouracil (5-FU), wherein the 5-FU is administered at a dosage within the range of about 0.1-1000 mg per dosage unit.

Methylol transfer agents, such as the antibacterial and antitoxin drug taurolidine and the related product taurultam, have been shown to exert a modifying effect on the toxicity of tumor necrosis factor (TNF) which is used, inter alia, in the treatment of tumors. Furthermore, the action of methylol transfer agents has been shown to be selective in that the growth of normal cell-lines was not significantly inhibited.

Taurolidine acts by transferring three methylol groups at the site of action, taurultam being an intermediate metabolite which itself transfers a single methylol group with liberation of the very well tolerated compound taurinamide. Thus, the two compounds act by essentially the same mechanism. It should be noted that methylol transfer is to be contrasted with methyl transfer which is characteristic of many highly toxic anti-tumor drugs. Taurolidine and taurultam have low toxicity and are not cytotoxic against normal cells.

Programmed cell death is an evolutionary conserved biological principle in the regulation of cell numbers. Sensitive cells contain death receptors which are activated when the appropriate ligands are secreted from neighboring cells. A prominent system in programmed cell death is Fas-ligand mediated apoptosis. Fas, also known as CD 95/APO-l, is a cell surface receptor and a member of the tumor necrosis factor receptor superfamily which mediates apoptosis in sensitive cells upon oligomerization by the Fas-ligand (FasL).

In accordance with one embodiment, a method of treating cancer is provided, whereby apoptotic death of a neoplastic cell is induced by contacting said cell with an apoptosis-inducing amount of a methylol-containing compound.

One embodiment comprises administration of a methylol transfer agent in at least two dosing cycles, each cycle comprising an administration phase and a non-administration (rest) phase, the administration phase comprising administration, preferably by infusion, of a daily dose of the methylol transfer agent for about 1 to 8 days, followed by a non-administration (rest) phase of about 1 to 14 days during which no methylol transfer agent is administered.

In another embodiment, liver cancer is treated by intravenous infusion of solutions containing a methylol transfer agent, by direct administration through a catheter installed into a hepatic vessel, such as the hepatic artery, the portal vein, or the gastroduodenal artery.

In another embodiment, tumors of the central nervous system, such as glioma/glioblastoma, are treated.

Preferred methylol transfer agents are taurolidine, taurultam, and mixtures thereof.

One embodiment relates to the ability of methylol transfer agents, such as taurolidine, to induce cell toxicity, and to enhance Fas-ligand mediated apoptosis in combination therapy. Both taurolidine and its congener taurultam enhance the apoptotic effect of Fas-ligand in cancer cells at drug concentrations which per se show practically no effect on cell viability. In the human malignant glioma cell line LN-229 cell viability was reduced directly following incubation with taurolidine or taurultam alone. This effect enhanced the destruction of LN-229 cells by Fas-ligand. Thus, the use of methylol transfer agents to induce apoptotic cell death provides a means for treating cancer.

The two cell lines LN-18 and LN-229 represent validated model systems for apoptotic cell death with different sensitivities to Fas-ligand. These cell lines were therefore used to test the potential interaction of such compounds with the apoptotic pathway. The viability of the human malignant glioma cells LN-18 and LN-229 is differently affected by taurultam and taurolidine. The LN-18 cells, which are highly sensitive to Fas-ligand induced apoptosis, remained unaffected by taurultam at all concentrations tested (5, 20, 100 µg/ml) (Example 6). Taurolidine was able to only slightly reduce the viability of LN-18 cells at the highest concentration tested (100 µg/ml). Thus, the threshold for the destruction of LN-18 cells was reached at 0.01% of taurolidine. In contrast, LN-229 cells showed a much higher sensitivity to these drugs. In contrast to LN-18 cells, both taurultam and taurolidine by themselves (100 µg/ml) strongly decreased the viability of LN-229 cells. Taurolidine (100 µg/ml) caused a dramatic death of LN-229 cells (70%) and taurultam (100 µg/ml) was able to reduce the viability of LN-229 cells by 30%. At the highest concentration tested (100 µg/ml), taurolidine alone was about as effective as the Fas-ligand in inducing cell death. Thus, taurolidine and taurultam have the ability to destroy human malignant cells.

One method is carried out by administering to a mammal suffering from cancer, compositions containing an active methylol-containing compound, at a dose sufficient to induce death of neoplastic cells by apoptosis. By "methylol transfer agent," is meant a compound which contains or is capable of producing a methylol molecule under physiological conditions. A methylol-containing compound is characterized as having a R—CH2-OH group in which R is an alkyl, aryl or hetero group. The invention also includes the use of compounds capable of producing or being converted into a compound containing a R—CH2-OH structure.

Methylol transfer agents include methylol-containing compounds such as taurolidine and taurultam, and their derivatives. The compounds taurolidine and taurultam are disclosed in U.S. Pat. No. 5,210,083. Other suitable methylol-containing compounds include taurinamide derivatives and urea derivatives. Examples of derivatives of taurolidine, taurultam, taurinamide and urea useful in the present invention can be found in WO 01/39763A2. Particularly preferred methylol transfer agents for utilization in accordance with the present invention are taurolidine, taurultam, biologically active derivatives thereof and mixtures thereof.

Alternatively, the compound is a taurinamide derivative, or a urea derivative. Examples of derivatives of taurolidine, taurultam, taurinamide and urea useful in the present invention can be found in WO 01/39763A2.

Other methylol-containing compounds suitable for inducing apoptotic death of cancer cells include but are not limited to 1,3,-dimethylol-5,5-dimethylhydantoin, hexamethylene tetramine, or noxythiolin. By derivative of taurolidine or taurultam is meant a sulfonamide compound which possesses at least 10% of the neoplastic activity of taurolidine or taurultam, respectively. A sulfonamide compound is one having a R2N—SO2R' formula. Derivatives of the compounds described herein may differ structurally from a reference compound, e.g., taurolidine or taurultam, but preferably retain at least 50% of the biological activity, e.g., induction of apoptotic cell death, of the reference compound. Preferably, a derivative has at least 75%, 85%, 95%, 99% or 100% of the biological activity of the reference compound. In some cases, the biological activity of the derivative may exceed the level of activity of the reference compound. Derivatives may also possess characteristics or activities not possessed by the reference compound. For example, a derivative may have reduced toxicity, prolonged clinical half-life, or improved ability to cross the blood-brain barrier.

Treatment of an autologous tumor, e.g., a tumor of the central nervous system (CNS), is carried out by administering to a mammal, e.g., a human patient, a methylol-containing compound. The compound is administered systemically, e.g., orally or intravenously, or infused directly to the site of the tumor, e.g., to the brain or cerebrospinal fluid. An erodible or resorbable solid matrix such as a wafer or sponge can be implanted directly into brain tissue.

Cancers to which the present invention may be applicable include glioma, neuroblastoma, astrocytoma, carcinomatous meningitis, ovarian cancer, prostate cancer, central nervous system (CNS) cancer, lung cancer, gastric cancer, esophageal cancer, urinary bladder cancer, leukemia, lymphoma, melanoma, renal cell cancer, mesothelioma and metastases thereof. Other cancers against which the method of the present invention is effective include other carcinomas, sarcomas or lymphomas, cancers of the head and neck, liver cancer, breast cancer and pancreatic cancer.

Some embodiments involve treatment of cancers selected from the group consisting of glioma, neuroblastoma, astrocytoma, central nervous system (CNS) cancer, and liver cancer, as well as inhibition of tumor metastases thereof.

It is particularly beneficial to use taurolidine and/or taurultam, at concentrations sufficient to induce apoptosis in cancer cells, to prevent the spread of metastases, especially following surgical removal of tumors. The mammalian subjects are typically humans.

The invention also includes the use of taurolidine and/or taurultam, at concentrations sufficient to induce apoptosis in cancer cells, for the treatment or prophylaxis of tumors in mammalian subjects.

The invention further includes the use of taurolidine and/or taurultam, at concentrations sufficient to induce apoptosis in cancer cells, for the preparation of pharmaceutical compositions for the treatment or prophylaxis of tumors in mammalian subjects by induction of apoptosis.

Effective dosage amounts of a methylol transfer agent in accordance with the present invention may comprise pharmaceutical dosage units within the range of about 0.1-1,000 mg/kg, preferably 150-450 mg/kg per day, and most preferably 300-450 mg/kg per day. Alternatively, the dosages can be administered on a grams/day basis, from about 2-60 g/day. Preferred doses may be in the range of about 2.5-30 g/day taurolidine, 4-60 g/day taurultam, or a mixture thereof. Most preferred doses are in the range of about 10-20 g/day taurolidine, 20-40 g/day taurultam, or a mixture thereof.

Suitable formulations for injection or infusion may comprise an isotonic solution containing one or more solubilizing agents, e.g., polyols such as glucose, in order to provide solutions of increased taurolidine or taurultam concentration. Such solutions are described in EP 253662B1. The concentration of taurolidine or taurultam in such solutions may be in the range 1-60 g/liter.

Methylol transfer agents are generally poorly soluble in water. Thus, it is often required to administer relatively large volumes of aqueous solutions containing taurolidine or taurultam, for example 10 g to 30 g of taurolidine and/or taurultam. Preferred solutions for administration in accordance with the present invention contain from about 0.5-2% taurolidine and/or taurultam. It may be convenient to administer these compounds by infusion in view of the relatively large volumes concerned, conveniently at intervals throughout the day.

Administration, preferably by infusion, of the total daily dose can be carried out at a consistent rate over 24 hours, or according to a more rapid infusion schedule of the dose in portions, with breaks between each portion of the dose, e.g. infusion of 250 ml of a 2% taurolidine solution (5 g dose) over 2 hours, followed by a brief break of 4 hours, repeated over the course of a 24 hour infusion period to achieve a total daily dose of 20 g. Alternatively, 250 ml of a 2% taurolidine solution may be infused over one hour, with a one hour break between dose portions, and repeated until the daily dose is achieved, such that the total daily dose is provided over the course of less than 24 hours (i.e., approximately half the day), with no infusion occurring during the remainder of the day.

In accordance with one embodiment, four bottles (250 ml each) of 2% taurolidine solution are administered intravenously to patients with cancer, at a rate of 40 drops per minute, one bottle every six hours. The therapy cycle generally is an administration phase of daily infusions for one week, followed by a rest phase of two weeks. Total treatment generally is at least two such cycles. Efficacy of taurolidine 2% solution administered intravenously has been found to be particularly good with 25-28 bottles of 250 ml taurolidine 2% solution being instilled per cycle.

In accordance with a second embodiment of the invention, the administration phase comprises a daily regimen whereby 250 ml of taurolidine 2% solution is administered over the course of 2 hours, followed by a four hour break, repeated over 24 hours to achieve the total daily dose.

In accordance with a third embodiment of the invention, the administration phase comprises a daily regimen whereby 250 ml of 2% taurolidine solution is infused over one hour, followed by a one-hour break, and repeated until the daily dose is achieved. If the total dose is 20 g (for example), this regimen would provide the daily dose with four 250 ml infusions of 2% taurolidine over a 7 hour time span. No infusion occurs for the remainder of the day. Infusion rates can be lengthened (e.g., to 250 ml over 90 or 120 minutes) if the patient shows an elevated liver count.

In some embodiments, patients are subjected to dosing cycles having an administration phase of at least 3 continuous days, and up to about 8 continuous days, each administration phase being followed by a non-administration phase of about 1 day to about 4 weeks, e.g., 1-14 days, or even 3, 4 or more weeks, during which the methylol-containing compound is not administered to the patient. During each administration phase, the methylol-containing compound is administered each day. For example, administration phases of 3, 4, 5, 6, 7 and/or 8 days can be utilized, and non-administration phases of 1, 2, 3, 4, 5, 6, 7, 8, 9, 10, 11, 12, 13, and/or 14 days may be utilized. At least 2 dosing cycles are utilized, preferably 5-10 or more dosing cycles are utilized. For example, 2, 3, 4, 5, 6, 7, 8, 9, 10 or more sequential dosing cycles can be utilized. Such a regimen has shown surprising and unexpected results with patients. In one embodiment, 6 dosing cycles, each with administration phases of 5 days are utilized, with each administration phase separated by a non-administration phase of 2 days. Preferably, during each day of administration, 250 ml of taurolidine 2% solution is intravenously administered to the patient 4 times daily. Such a regimen has surprisingly and unexpectedly resulted in a marked tumor size reduction with disappearance of perifocal edema in a patient with inoperable glioblastoma infiltration of the basal ganglia.

In another embodiment, a non-administration phase may be 1, 2, 3, 4 or more weeks in length, e.g., about 2-4 weeks. For example, in patients with recurrent cancers such as of the stomach and pancreas may be administered sequential dosing cycles having an administration phase of 3-8 continuous days, e.g., 7 days, with, for example, 250 ml taurolidine 2% solution infused 4 times daily, followed by a non-administration phase of 1, 2, 3, 4, or more weeks, e.g., 3 weeks. As in the previous embodiments, at least 2 dosing cycles are utilized, preferably 5-10 or more dosing cycles.

In a further embodiment, concomitant administration of anti-convulsants and/or anti-oedema therapy and/or antibiotics and/or fluid and electrolyte replacement is carried out.

1. Anti-Convulsants

The patient may be stabilized on anti-convulsive medications prior to treatment, to avoid complications during the treatment. This can conveniently be administered in part on an out-patient basis, as well as to prevent any emergency stabilization on an undesired medication. Valproinic acid is the agent of first choice; the dose should be determined in accordance with blood level checks and administered in 2 single doses. Normally, a dose of 1200 mg to 1500 mg is required. If a treatment with valproinic acid is not sufficient, a combination treatment with lamotrigin is possible. In case of allergies or if valproinic acid is not tolerated, the primary stabilization is to be done with lamotrigin. Phenytoin and carbamazepin are contra-indicated.

2. Anti-Oedema Therapy

An anti-oedema therapy may also be administered, but only if absolutely necessary, because otherwise focal neurological symptoms may occur or become intensified, or intracerebral pressure may symptoms develop. Dexamethason should be given before or after the taurolidine was administered. The anti-oedema therapy should be administered with dexamethason, using the lowest possible dose. To protect the stomach a concomitant therapy with ranitidine 1×150 mg/day may be given. If stomach problems are observed with this therapy, an alternative treatment with antra 1-2×20 mg/day should be administered.

In cases of massively elevated intracerebral pressure and insufficient effectiveness of dexamethason, a therapy with mannitol, in particular at a dosage of up to 4×250 ml/day, is possible.

3. Antibiotic Therapy

A calculated antibiotic treatment with one of the subsequently listed antibiotics may be given, until the arrival of the sensitivity test.

Urinary tract infection:
primary: Cotrimoxazol
alternative: Doxycyclin
Pneumonia:
primary: Erythromycin
alternative: Doxycyclin The following antibiotics should only be used if absolutely necessary (in the most severe, life-threatening infections) and if the sensitivity situation warrants it: Chino lone, penicillin, cephalosporin 4. Fluid and Electrolyte Replacement in Connection with Intravenous Taurolidine 2% Therapy An amount of 250 ml of full electrolyte solution is preferably be given at the same time and with the same infusion speed parallel to the infusion with 250 ml taurolidine 2%. Electrolytes and blood count should be monitored twice per day, and the central vein pressure should be checked once daily.

If a hypernatraemia is observed, first, it should be determined whether dehydration is the cause. Diuretic agents should only be used if fluid is replaced at the same time and after dehydration was ruled out as the reason.

The methylol-containing compound is administered alone or in combination with one or more additional antineoplastic agents. In one preferred embodiment, the supplemental agent kills tumors cells by a mechanism other than apoptosis. For example, an antimetabolite, a purine or pyrimidine analogue, an alkylating agent, crosslinking agent (e.g., a platinum compound), and intercalating agent, and/or an antibiotic is administered in a combination therapy regimen. The supplemental drug is given before, after, or simultaneously with the methylol-containing agent. For example, the methylol transfer agent can be co-administered with a fluoro-pyrimidine, such as 5-fluoro-uracil (5-FU). Effective daily dosage amounts of a fluoro-pyrimidine may be in the range of about 0.1-1,000 mg per pharmaceutical dosage unit. Effective dosage amounts of 5-FU also may be in the range of about 100-5,000 mg/m2 body surface area, preferably about 200-1,000 mg/m2 body surface area, more preferably about 500-600 mg/m2 body surface area. 5-FU typically is provided in 250 mg or 500 mg ampules for injection, or 250 mg capsules for oral administration.

In another embodiment, the apoptotic effect of methylol transfer agents can be enhanced by co-administration with a Fas-ligand. A Fas-ligand polypeptide is disclosed in U.S. Pat. No. 5,858,990. Therapeutically effective amounts of Fas-ligand generally will be within a range of about 0.01-1,000 mg/kg patient body weight, preferably about 0.1-200 mg 1 kg patient body weight, most preferable about 0.2-20 mg/kg patient body weight. The therapeutically effective amounts can be administered as dosages once per day, or multiple times per day such as two, three, four or more times per day.

In LN-18 cells taurultam (100 µg/ml) clearly enhanced apoptosis induced by 0.4 or 2.0 vol. % Fas-ligand. This is the more striking as taurultam by itself did not impair the cell viability at this concentration. Thus, taurultam is able to enhance the effectiveness of the Fas-ligand induced apoptotic pathway. The same holds for taurolidine (100 µg/ml), although taurolidine alone did reduce cell viability at this concentration. These results support the view that the apoptotic affect of taurultam and taurolidine is enhanced by Fas-ligand. When taurultam or taurolidine at a concentration of 100 µg/ml are combined with Fas-ligand, the total cell loss represents itself as the sum of that of Fas-ligand and of taurolidine or taurultam alone. Thus, the cytotoxicity of taurultam and taurolidine at this concentration appears to be additive to the Fas-mediated apoptosis. At lower concentrations, the apoptopic effect of taurolidine and taurultam are greatly enhanced, beyond an additive effect, by co-administration with the Fas-ligand.

The invention also includes treating a drug resistant tumor, e.g., a multiple drug resistant (MDR) tumor, in a mammal by administering to the mammal a methylol-containing compound. The tumor to be treated is a carcinoma or sarcoma. The drug resistant tumor is selected from the group consisting of a solid tumor, a non-solid tumor, and a lymphoma. For example, the drug resistant tumor is a breast cancer, ovarian cancer, colon cancer, prostate cancer, pancreatic cancer, CNS cancer, liver cancer, lung cancer, urinary bladder cancer, lymphoma, leukemia, or sarcoma.

According to another embodiment, a solution containing taurolidine and/or taurultam further contains taurin, in an amount within a range of about 1-20 g/l, preferably about 5 g/l.

A further embodiment provides methods for treating both primary liver tumors and metastases thereof, by direct administration of a solution containing a methylol transfer agent to the liver through a catheter installed in a hepatic vessel. By administering the methylol transfer agent in a solution that assists in maintaining liver function and non-ischemic conditions, therapy is directed to the affected organ, without unduly subjecting the organ to undue stress.

For treatment of primary liver tumors, the solution of methylol transfer agent may be administered through the hepatic artery, such that the therapeutic agent is carried into the organ for maximum effect. Alternatively, the solution can be supplied via the gastroduodenal artery, for delivery to the liver through the hepatic artery. The preferred solution for use in this embodiment is one that assists in maintaining liver function and minimizing stress to the organ associated with infusion of large volumes of methylol transfer agent solution. Solutions which may be used in the present invention are set forth in the Examples.

The following non-limiting examples serve to further illustrate the invention.

EXAMPLE 1

To prevent intraperitoneal tumour growth and trocar metastases caused by laparoscopic operations, the effect of taurolidine and heparin were investigated on the growth of colon carcinoma cells (DHD/L12/TRb) in vitro, as well as in rat models. After incubation of the cells with heparin, taurolidine or both substances there followed the in vitro determination of the growth kinetics of the cells. A second experiment followed on rats (n=60) following intraperitoneal application of tumour cells and subsequently the development of a pneumoperitoneum for 30 mins. The rats were randomised into 4 groups:
I Tumour cells
II Tumour cells+heparin
III Tumour cells+taurolidine
IV Tumour cells+taurolidine+heparin
Results Where the tumour growth in vitro was not affected by heparin, a significant suppression of growth was observed with taurolidine and taurolidine/heparin. In vivo, however, the intraperitoneal tumour weight compared to the control group (596.+−0.278 mg) was reduced both with the instillation of heparin (298.+−0.155 mg) as well as with taurolidine (149.+−0.247 mg). The combination of both substances caused a further average tumour weight reduction of (21.5.+− 0.36 mg). The development of trocar metastases could be significantly suppressed using either taurolidine alone, or the combination of taurolidine and heparin.

EXAMPLE 2

Laparoscopic Procedure

In a typical abdominal procedure, which should not be considered as limiting, a 0.5% taurolidine Ringer solution at body temperature is rinsed through the suction rinse tube under minimal pressure intra-operatively.

According to the extent of surgical invasion, from 100-250 ml 2% taurolidine is instilled at 37° C. and allowed to remain in the abdominal cavity on conclusion of the operative procedure.

EXAMPLE 3

Laparoscopic Procedure

A typical abdominal procedure may be carried out in accordance with Example 2, except that the 2% taurolidine solution is replaced by a 500 ml 0.5% taurolidine Ringer solution used in combination with 2500 I.U. heparin. This solution is instilled into the abdominal cavity via drains which are then clamped for 2 hours.

EXAMPLE 4

Laparotomy

Partial Pancreatectomy

In a typical treatment of pancreas head carcinoma, the operation site is meticulously rinsed with approx. 500-1000 ml warm (37° C.) 0.5% Taurolin-Ringer solution. After 10 minutes contact time, the solution is suctioned off.

Every 20 minutes the operation site is moistened with 100-200 ml 2% Taurolin solution using a large calibrated curved syringe.

After 10-15 minutes contact time the solution is suctioned off. Before final closure of the abdominal wall, 250 ml Taurolin 2% solution* (with heparin added according to the blood coagulation results) is instilled.

*Alternatively, 2-3% taurultam may be used.

EXAMPLE 5

Laparotomy

Radical Mastectomy

In a typical treatment of mamma carcinoma (radical mastectomy), the operation site is rinsed intra-operatively every 20 minutes using 200 ml Taurolin 2% solution. If possible, a 10 minute contact time is permitted by lifting the surgical drapes thereby preventing the rinse solution from draining away too quickly.

The operation wound is then closed and drained.

Additionally, intraoperative per drop infusion of 250 ml 2% Taurolin solution is administered via a central catheter (dosage: 4×250 ml per 24 hours).

EXAMPLE 6

Laparoscopic Procedure

In a typical abdominal procedure, a taurolidine solution is administered in the form of an aerosol. This may be achieved through the use of a micro-pump which is situated between a gas (e.g. $CO_2$) supply and the abdominal cavity in which surgery is to be performed. A tube is used to carry the aerosol into the trocar tube or sleeve. The taurolidine solution may be administered continuously as a spray during abdominal surgery, e.g. at a rate of 100 to 200 ml per hour.

EXAMPLE 7

Patients were treated in accordance with the following therapy regimen. Month 1, days 1-7, 2% taurolidine solution administered intravenously 4 times daily (300 mg/kg per day), followed by a three week therapy pause (non-administration phase). Month 2, days 29-36, 2% taurolidine solution administered intravenously 4 times daily as above, followed by three week therapy pause. Month 3, days 56-63, 2% taurolidine solution administered intravenously 4 times daily as above, followed by a three week therapy pause. Month 4, days 84-91, 2% taurolidine solution administered intravenously 4 times daily, as above followed by a three week therapy pause. Month 5, days 112-119, 2% taurolidine solution administered intravenously 4 times daily, as above, followed by a three week therapy pause. Month 6, days 140-147, 2% taurolidine solution administered intravenously 4 times daily, as above, followed a three month therapy pause.

In this study, 13 patients were treated, including 3 patients with liver metastasis and 7 patients with liver insufficiency (decompensated liver function or substantial liver failure). Patients with liver metastasis included infiltration of stomach tumors into adjacent structures, including liver. Patients with liver insufficiency included those due to cancer of the head of pancreas and progressive carcinoma of the caecum, primary and recurrent cancer of the cardiac part of the stomach, carcinoma of kidneys and prostate. Five patients showed remission and stabilization with normalization of tumor markers, improved quality of life, no adverse events, no liver impairment and an extension of survival time (median 8 months). This compares favorably against survival of similar patients treated in accordance with known Gemcitabin (Gemzar®, Lilly) treatment, wherein pancreatic carcinoma patients with liver metastasis have a survival time of about 1 month, and gastric cancer patients with liver metastasis have a survival time of about three months. Moreover, the adverse events of treatment with prior art Gemcitabin include severe liver damage, myelosuppression, and influenza-like syndrome.

Accordingly, taurolidine is highly effective in liver metastases of cancers such as peritoneal carcinosis, and taurolidine may be even be used in patients with liver insufficiency, including decompensated liver function or substantial liver failure.

EXAMPLE 8

Cancer patients are selected who are undergoing major abdominal cancer surgery. Two groups are patients are studied. Group A receives 250 ml taurolidine 2% solution drop infusion for two hours, followed by two hour intervals, a total of four times for a total administration of 1 liter taurolidine 2% solution. The taurolidine solution is administered intravenously through a central line prior to surgery. Group B receives saline vehicle control according to the same schedule. Taurolidine 2% solution is administered for two further doses post-operatively at six hour intervals. Antibiotic profolacts cover is given as Augmentin 1.2 g at induction and a further two doses given post-operatively. The effects of taurolidine 2% solution administered intravenously to cancer patients including colon, rectum, pancreas, stomach and lung cancer patients on angiogenic growth factors were as follows.

Reduction in serum vascular endophileo growth factors (VEGF) from 500-600 µg/ml to 350-360 µg/ml. Reduction of serum transforming growth factor (TGF-β) from 2,300-2,350 µg/ml to 990-1,050 µg/ml six hours post-operatively and 1,700 µg/ml 24 hours post-operatively. Taurolidine 2% solution administered intravenously also decreased serum soluble adhesion molecules following surgery in cancer patients, including sE-selectin, sP-selectin and sVCAM-1.

EXAMPLE 9

The effect of Taurolidine was examined on the growth of a rate metastatic colorectal tumor cell line (DHD/K12/TRb) in vitro and in vivo.

In the in vitro experiments, DHD/K12/TRb cells were incubated with 5, 10, 15, 25 µg/ml of Taurolidine. Cells incubated in culture medium alone were used as controls. Cell proliferation, cell viability, cell death, and cell apoptosis were measured using commercially available techniques.

In the in vivo experiment, BD IX rats were randomized into 2 groups (n=10/group). Group A (control) underwent laparotomy, instillation of DHD/K12/TRb tumor cells intraperitoneally followed by phosphate buffered saline (PBS). Group B received Taurolidine (100 mg/kg) instead of PBS. Animals were sacrificed after 24 days and tumor burden assessed by counting the number of tumor nodules in the peritoneal cavity.

Incubation of the tumor cells with Taurolidine resulted in a 4 fold decrease in proliferation rates (25±4% v 100±28% for controls) and a 4 fold increase in cell necrosis as demonstrated by the increase in LDH release (403±28% v 100±26% for controls), at a Taurolidine concentration of 25 µg/ml. A dose dependent decrease in cell viability was also observed. In the in vivo study, local Taurolidine administration resulted in significant decreases in tumor burden (3±1 nodules in Group B animals vs 649±101 nodules in Group A animals). Taurolidine thus inhibits the growth of a rat metastatic colorectal tumor cell line in vitro and in vivo and prevents or reduces peritoneal metastates.

EXAMPLE 10

The human colon cell lines SW 480 (primary), SW 620 (metastatic) and W 707 (metastatic) were incubated with the following: culture medium (control), taurolidine at 5, 10, 25, 50 and 100 µg/ml doses, and 5-Fluorouracil (5-FU) at 5, 10, 25, 50 and 100 µM doses. Cell proliferation, apoptosis and cell cycle were assessed.

There was a significant decrease in tumor cell proliferation at 24 hours as shown in the table (results as % of control). There was no significant increase in taurolidine-induced apoptosis and taurolidine did not alter the phases of the cell cycle. There was an increase in LDH release (p=0.0011), which correlated with inhibited tumor proliferation. Taurolidine was also compared with 5-FU and was found to be superior in inhibiting cell proliferation (p=0.001) and augmented the effects of given doses of 5-FU (p=0.0001).

| PROLIFERATION | Control | T 5 µg/ml | T 10 µg/ml | T 25 µg/ml | T 50 µg/ml | T 100 µg/ml | |
|---|---|---|---|---|---|---|---|
| SW 480 | 100 | 100.10 ± 0.18 | 101.68 ± 2.17 | 87.93 ± 2.95* | 53.55 ± 3.84* | 14.62 ± 4.40* | p = .0001 |
| SW 620 | 100 | 89.42 ± 1.85 | 90.22 ± 1.55 | 58.10 ± 14.86* | 25.01 ± 8.87* | 7.8 ± 1.35* | p = .0001 |
| SW 707 | 100 | 97.33 ± 4.06 | 88.48 ± 9.39 | 62.37 ± 24.27 | 36.81 ± 15.36* | 6.02 ± 0.26* | p = .0009 |

ANOVA (*vs controls)

Taurolidine inhibits the proliferation of these three human colon cell lines at doses within the therapeutic range and proved to be more effective than the above doses of 5-FU and it also enhanced the effects of 5-FU. It would appear to act as a direct cytotoxic agent on the tumor cells.

EXAMPLE 11

Isotonic Solution 2% Taurolidine

One suitable composition for intravenous drop infusion is shown below.
Isotonic sterile solution, 100 ml:
2.0 g Taurolidine
5.0 g PVP 16 PF UP aqua dest. ad solut. 100 ml. PH 7.2-7.3
Sterile-filtered and steam sterilization.

EXAMPLE 12

Isotonic Solution 2% Taurolidine with Taurin and Electrolytes

Another suitable composition for intravenous drop infusion is shown below.
Isotonic sterile solution, 100 ml:
2.0 g Taurolidine
5.0 g PVP 17 PF UP 0.5 g Taurin
0.3 g Sodium chloride
Sterile-filtered and steam sterilization

EXAMPLE 13

Isotonic Ringer Solution 2% Taurolidine with Taurin and Electrolytes

Another suitable composition for intravenous drop infusion is shown below.
Isotonic sterile solution, 100 ml:
2.0 g Taurolidine
5.0 g PVP 17 PF UP
0.5 g Taurin
0.26 g Sodium chloride
0.0033 g Potassium chloride
0.004 g Calcium chloride 2H2O
0.003 g Sodium hydrogen carbonate
Sterile-filtered and steam sterilization

EXAMPLE 14

Ringer-Lactate 2% Taurolidine with Taurin and Electrolytes

Another suitable composition for intravenous drop infusion is shown below.
Isotonic sterile solution, 100 ml:
2.0 g Taurolidine
5.0 g PVP 17 PF UP
0.5 g Taurin
0.20 g Sodium chloride
0.013 g Potassium chloride
0.009 g Calcium chloride 2H2O
0.0033 g Sodium lactate 50% solution (Pharmacopeia Europea)
Sterile-filtered and steam sterilization

EXAMPLE 15

Taurultam Solution

One preferred solution comprises:

| | |
|---|---|
| Lactobionic acid | 35.830 g |
| Adenosine | 1.340 g |
| Raffinose Pentahydrate | 17.830 g |
| Hydroxyethyl starch (HES) PL 40/0.5 | 50.000 g |
| Glutathione | 0.929 g |
| Allopurinol | 0.136 g |
| Taurultam | 10.000 g |
| Kcl | 5.200 g |
| MgS04 7H2O | 1.230 g |
| NaOH 25% GV to pH 7.8 | |
| NaOH pellets Merck 6482 | |
| Distilled water | 900 ml |

The solution was sterilized from 16 minutes at 121° C. The pH after sterilization was 7.2, and pH of ready to use solution was 7.47.

EXAMPLE 16

Inducement of Apoptosis

Taurolidine and taurultam were tested for their ability to enhance apoptosis or induce cell death, alone and in combination with the Fas-ligand, in human malignant glioma cell lines. The two cell lines LN-18 and LN-229 represent validated model systems for apoptotic cell death with different sensitivities to Fas-ligand (Schlappbach and Fontana, 1997). These cell lines were therefore used to test the potential interaction of taurultam or taurolidine with the apoptotic pathway.

1) Reagents

Taurolidine (Batch Nr. 41692/7) and taurultam (Batch E/39024/4) were provided by Geistlich Pharma AG, Wolhusen, Switzerland. DME-Culture Medium and fetal bovine serum (FBS) were purchased from Gibco BRL, Basel, Switzerland. The cell proliferation assay WST-1 was purchased from Roche Diagnostics, Rotkreuz, Switzerland. Fas-ligand (supernatant from an overexpression system) and the human glioma cell lines LN-18 and LN-229 were kindly provided by Prof. A. Fontana, Institute of Clinical Immunology, University Hospital, Zurich, Switzerland 2) Cell Lines The cell lines LN-18 and LN-229 were cultured at 37° C. and 5% $CO_2$ in DMEM containing 5% FBS and 2 mM glutamin (10 cm plates NUNCLON 15035). In the experiments in which Fas-ligand was tested by itself, about 1×104 cells were plated per well in 96-well plates (NUNCLON 167008) resulting in a confluency of about 60% on the following day (17 h incubation). In all other experiments about 1.5×104 cells were plated which resulted in a confluency of about 90% on the following day (17 h incubation). Fas-ligand was added as supernatant indicated as % volume (vol %) of total culture volume.

3) Cell Viability Test

LN-18 and LN-229 cells were incubated in 50 µl medium in the absence or presence of either Fas-ligand, taurultam, taurolidine or respective combinations thereof. After a 17 h incubation the cell viability was determined by adding 50 µl medium containing a double concentrated WST-1 reagent. The coloration resulting from the activity of the mitochondrial succinate reductase, was measured in an ELISA reader at 450 nm using a reference wavelength of 690 nm.

The human malignant glioma cell lines LN-18 and LN-229 were used to test the ability of taurolidine and taurultam to affect cell viability and/or to enhance Fas-ligand induced apoptosis. The two human malignant glioma cell lines, LN-18 and LN-229 had previously been reported to display different sensitivity to the apoptotic effect of Fas-ligand (Schlappbach and Fontana, 1997).

1) Sensitivity of LN-18 and LN-229 to Fas-Ligand

In a first set of experiments it was investigated whether the different sensitivity of LN-18 and LN-229 to Fas-ligand was reproduced under our experimental conditions. The two cell lines were incubated over night (17 h) in 96 well plates containing 1×104 cells per well with increasing concentrations of Fas-ligand (3.1, 6.25, 12.5, 25.0 and 50 vol. %). In the absence of Fas-ligand the cells reached about 60% confluency after overnight incubation. In the presence of Fas-ligand LN-18 was extremely sensitive, displaying more than 90% loss of cell viability in the presence of only 6.25 vol. % Fas-ligand. Even at 3.1%, an approximately 85% reduction in cell viability was observed. In contrast, the viability of LN-229 cells was not greatly affected by 6.25 vol. % Fas-ligand (approximately 10% reduction) and was reduced only at higher concentrations with a maximum of 40% cell loss in the presence of the highest concentration of Fas-ligand tested (50 vol. %).

2) Influence of Taurultam on Fas-Ligand Induced Apoptosis in LN-18-Cells

LN-18 cells were incubated for 17 h with increasing concentrations of taurultam (5, 20, 100 µg/ml) in the absence and presence of two concentrations of Fas-ligand (0.4 vol. % and 2.0 vol. %). Taurultam by itself even at the highest concentration tested (100 µg/ml) did not affect the cell viability (an approximately 5% reduction was observed at 5 and 20 µg/ml, and viability actually appeared to increase at 100 µg/ml). In the presence of 0.4 vol. % Fas-ligand alone cell viability was reduced by only about 10%, an effect which remained unchanged in the presence of 5 or 20 µg/ml taurultam. However cell viability was strongly decreased when 0.4 vol. % Fas-ligand was coincubated with of 100 µg/ml taurultam. When the Fas-ligand was added at a higher concentration (2.0 vol. %) apoptosis was induced in 60% of the cells by Fas-ligand alone. This effect was also increased by taurultam at 100 µg/ml but not at 5 or 20 µg/ml. Thus, taurultam is able to enhance the apoptotic effect of Fas-ligand in LN-18 cells at a concentration (100 µg/ml) which by itself did not affect cell viability.

3) Influence of Taurolidine on Fas-Ligand Induced Apoptosis in LN-18 Cells

LN-18 cells were incubated for 17 h with either 0.4 or 2.0 vol. % Fas-ligand in the absence and presence of increasing concentrations of taurolidine (5, 20, 100 µg/ml). Taurolidine by itself did not appreciably affect cell viability yielding a reduction by only 10% at the highest concentration tested (100 µg/ml). In the presence of Fas-ligand alone (0.4% or 2.0%) the cell viability was affected in the same way as described above. The cell viability was further reduced by taurolidine but only at the highest concentration tested (100 µg/ml). Thus, taurolidine was able to enhance the effect of Fas-ligand on LN-18 cells at a concentration (100 µg/ml) which did not appreciably affect cell viability per se.

4) Influence of Taurultam on Fas-Ligand Induced Apoptosis in LN-229 Cells

The incubation of LN-229 cells for 17 h with taurultam alone had no effect at 5 and 20 µg/ml but reduced cell viability by 35% at 100 µg/ml. When the LN-229 cells were incubated with Fas-ligand alone (10% or 50%) the cell viability was reduced by only about 20% in the presence of a high concentration of Fas-ligand (50 vol. %). When taurultam was added at concentrations which were inactive per se (5 and 20 µg/ml) no change in the effectiveness of the Fas-ligand (10 or 50 vol. %) was observed. It was only at the highest concentration of taurultam (100 µg/ml) that Fas-ligand induced cell loss was further enhanced. Thus, the results with LN-229 demonstrate the ability of taurultam to enhance the destruction of cells in the presence of Fas-ligand.

5) Influence of Taurolidine on Fas-Ligand Induced Apoptosis in LN-229 Cells

The exposure of LN-229 cells to taurolidine alone for 17 h caused a strong loss of cell viability by about 70% at the highest concentration tested (100 µg/ml). Thus, LN-229 cells were more sensitive to taurolidine than LN-18 cells. When co-incubated with Fas-ligand (10 vol. %) cell destruction was enhanced by taurolidine at 100 µg/ml. At 50 vol. % Fas-ligand the effect was more pronounced and apparent even for taurolidine 20 µg/ml.

EXAMPLE 17

Use and Application of Taurolidine and/or Taurultam for the Treatment and/or Prophylaxis of Tumors of the Central Nervous System 1. Tumor Cells Used for the Experiments For experiments, C6 glial tumor cells, HT22 neuronal tumor cells, U373 human glioma/glioblastoma tumor cells and cells derived from patients with glioblastoma were used.

2. Preparation of Patient-Derived Tumor Cells

Tumor cells derived from patients with glioblastoma were obtained intraoperatively. Tumor tissue was stored in RPMI 1640 medium without FCS. Tissue was then sub cultured in 15 ml Falcon flasks; adding 0.025% trypsin with PBS, followed by incubation at 37° C. After this, RPMI 1640 with FCS was added and centrifugation performed. The next step was incubation with DNAse, resuspension and dissociation, followed by washing step in medium to remove DNAse. Cells were then cultured in Falcon flasks.

3. Method of Anti-Neoplastic Action of Taurolidine and/or Metabolites

Ultrastructurally, shrinkage of cytoplasm, condensation and marginalization of chromatin could be observed. These changes were already apparent at 30 minutes of incubation with 0.1 µg/ml taurin and increased strikingly over time and with concentration of taurolidine. Mitochondria were not affected ultrastructurally. Flow cytometry showed an initial increase in the G0/G1 peak and S-phase starting at 30 minutes. These initial changes were followed by a decrease in forward light and side scatter. In addition, concentration-dependent fragmentation of DNA started at 60 minutes. Following 24 hours, fragmentation of the DNA was nearly complete. At concentrations of 2.0 µg/ml taurolidine and more, the changes in cell size was only marginal.

The described results in combination with the results of special dying methods (Leucostat preparation) suggests an apoptotic mechanism of tumor cell death. Normal brain cells were not affected by incubation with taurolidine or taurultam in concentrations of up to 4 µg/ml for up to 5 days.

EXAMPLE 18

Two-Cycle Dosing Schedule for Treating Patients with Cancer Using Intervenous Taurolidine 2%

Four bottles (250 ml each) of 2% taurolidine solution are administered intravenously to patients with cancer, at a rate of 40 drops per minute, one bottle every six hours. The dosing cycle consists of an administration phase of daily infusions for one week, followed by a non-administration phase of two weeks, then followed by another administration phase of four bottles per day as previously indicated. Efficacy of taurolidine 2% solution administered intravenously has been found to be particularly good with 25-28 bottles of 250 ml taurolidine 2% solution being instilled per cycle.

EXAMPLE 19

Four-Cycle Dosing Schedule for Treating Patients with Malignant Gliomas Using Intravenous Taurolidine 2%

The treatment comprises a minimum of 4 cycles. Each cycle is 7 days long, and is comprised as follows:
1. First Cycle
 a. Intravenous infusion of 250 ml taurolidine 2% and 250 ml full electrolyte solution via the central vein catheter with an infusion time of 60 minutes.
 b. If this therapy causes an elevated liver count, it is necessary to increase the infusion time to 90 or 120 minutes.
 c. 60-minute break
 d. Repeat the therapies under a or b and c for a total of 6 times per day.
 e. At an infusion time of 60 minutes the duration of the daily infusion program per 250 ml of taurolidine is 11 hours, at 90 minutes of infusion time 14 hours, and at 120 minutes of infusion time 17 hours. No drug is administered for the remainder of the time.

f. rest phase

2. Subsequent Cycles a. Intravenous infusion of 250 ml taurolidine 2% and 250 ml full electrolyte solution via the central vein catheter with an infusion time of 60 minutes.

b. If this therapy causes an elevated liver count, it is necessary to increase the infusion time to 90 or 120 minutes.

c. 60 minute break d. Repeat the therapies under a or b and c for a total of 4 times per day.

e. At an infusion time of 60 minutes the duration of the daily infusion program per 250 ml of taurolidine is 7 hours, at 90 minutes of infusion time 9 hours, and at 120 minutes of infusion time 11 hours. No drug is administered for the remainder of the time.

EXAMPLE 20

Therapy of Glioblastoma with Taurolidine (Single Case Observation)

The following is a case involving treatment of a single individual with a single treatment cycle.

Patient: "F.D.," male, 59 years

Diagnosis: large (8×8×8 cm) malignant glioma bifrontal with affection of the corpus callosum ("butterfly glioma").

Procedure prior to treatment with taurolidine: Patient was referred to Neurosurgical departments in Heidelberg and Wurzburg, operation was refused, radiation and chemotherapy were refused by the patient.

Prior treatment: oral corticosteroids.

Planned Treatment: Taurolidine intravenously

Chief complaints on admission: Diffuse headache, urinary incontinence, blurred vision, motor aphasia, gait disturbance, impaired memory.

Neurological examination on admission: Awake-somnolent, alert, impaired vision, nearly complete motor aphasia, apraxia, gait disturbance, urinary incontinence, severe mnesic and concentration deficits Karnofsky index on admission: 20-30

MRI at Day 1 of treatment (pre treatment): Bifrontal space occupying lesion (ca. 8×8×8 cm) with irregular shape and ring like contrast enhancement and destructive affection of the corpus callosum. The marked space occupying effect leads to disappearance of nearly all reserve spaces.

Treatment

Day 1: Informed consent; Blood samples; MRI.

Day 2: Insertion of a central venous line; Chest X-ray.

Days 3-8: Intravenous administration of 4×250 ml of 2% taurolidine/day within 2 hours, followed by an interval of 4 hours; Blood samples twice daily; Substitution of electrolytes.

Day 9: Intravenous administration of 1×250 ml of 2% Taurolidine within 2 hours; Discharge.

Treatment summary:

In total, 25×250 ml of 2% taurolidine (125 g taurolidine) were administered without side effects. Electrolytes and fluid were substituted according to the results of the blood samples.

Chief complaints on discharge: Headache improved, no urinary incontinence, vision improved, gait disturbance improved, motor aphasia slightly improved, impaired memory.

Neurological examination on discharge: Awake, alert, vision improved, motor aphasia slightly improved, gait disturbance improved, apraxia slightly improved, no urinary incontinence, severe mnesic and concentration deficits Karnofsky index on discharge: 40-50

In view of the dramatic improvement observed in the patient's condition after a single treatment cycle, it is expected that an infusion regime of at least two cycles will provide the desired therapeutic effect. orientation as well as T1-weighted picture sequence in axial layer orientation natively and in axial, coronary and sagittal layer orientation after contrast medium application as well as MR spectroscopy.

The patient was treated with four treatment cycles each consisting of a seven-day infusion phase of a daily dose of 20 g taurolidine (4×250 ml 2% taurolidine solution) and a two-day rest phase. After the four cycles, the patient underwent an additional two-day infusion phase. Regular computer tomography images of the patient's cranium were taken during treatment.

By the end of the second treatment cycle (200 g taurolidine administered), brain edema was noticeably reduced. By the end of third treatment cycle (300 g taurolidine administered), tumor growth had stopped. After the completion of the entire course of treatment (600 g taurolidine administered), the tumor was shown by computer tomography to be almost completely disintegrated. Little or no necrosis was observed during the course of treatment, indicating that the tumor reduction was the result of apoptosis.

EXAMPLE 22

Treatment of Brain Tumors with Direct Application of Taurolidine/Taurultam

The methylol transfer agent is applied directly to the tumor cavity using taurolidine/taurultam containing tubes consisting of several segments with semipermeable membrane.

Following total or partial tumor removal, a special tube is implanted in the tumor cavity, so that the end of this tube lies subgaleal. The tube includes various segments of semipermeable material, which contains taurolidine/taurultam and can be refilled via a subgaleal port.

EXAMPLE 23

Treatment of Inoperable Glioblastoma Infiltration of Basal Ganglia

A forty year old male patient with inoperable glioblastoma infiltration in the basal ganglia was treated with a regimen of 6 dosing cycles, each with administration phases of 5 days, with each administration phase separated by a non-administration phase of 2 days. During each day of administration, 250 ml of taurolidine 2% solution was intravenously administered to the patient 4 times daily. This regimen surprisingly and unexpectedly resulted in a marked size-reduction of the tumor, and disappearance of perifocal edema.

The invention claimed is:

1. A method of treatment for reducing growth or spread of a liver tumor in a patient, comprising administering to said patient an effective amount of taurolidine, taurultam or a mixture thereof, so as to reduce growth or spread of said tumor in said patient wherein said administering includes instilling a solution of said taurolidine, taurultam or mixture thereof into said patient and further comprising administering to said patient a therapeutically effective amount of a Fas-ligand polypeptide.

2. The method of claim 1 wherein said liver tumor is a tumor metastasis.

3. The method of claim 1 wherein said taurolidine, taurultam or a mixture thereof is administered as a solution to said patient.

4. The method of claim 3 wherein said solution comprises about 0.5-2% by weight taurolidine, or about 2-3% by weight taurultam.

5. The method of claim 4 wherein said solution comprises about 0.5-2% by weight taurolidine.

6. The method of claim 1 further comprising administering intravenously to said patient a solution comprising taurolidine, taurultam or a mixture thereof.

7. The method of claim 6 wherein about 250 ml said solution is administered intravenously to said patient.

8. The method of claim 6 wherein about 250 ml said solution is administered to said patient intravenously about four times daily.

9. The method of claim 1 wherein said therapeutically effective amount of a Fas-ligand polypeptide is about 0.01 mg/kg to about 1000 mg/kg.

10. The method of claim 9 wherein said therapeutically effective amount of a Fas-ligand polypeptide is about 0.1 mg/kg to about 200 mg/kg.

11. The method of claim 9 wherein said therapeutically effective amount of a Fas-ligand polypeptide is about 0.2 mg/kg to about 20 mg/kg.

* * * * *